United States Patent [19]

Miller

[11] 4,182,322
[45] Jan. 8, 1980

[54] HEAD HARNESS DEVICE

[76] Inventor: Larry C. Miller, 465 Olivetta Pl., La Canada, Calif. 91011

[21] Appl. No.: 931,168

[22] Filed: Aug. 4, 1978

[51] Int. Cl.$^2$ .............................................. A61F 13/00
[52] U.S. Cl. ................................. 128/133; 128/76 R
[58] Field of Search ..................... 128/133, 134, 76 R, 128/132 R; 5/338

[56] References Cited

U.S. PATENT DOCUMENTS

| | | | |
|---|---|---|---|
| 3,358,141 | 12/1967 | Hoffmann et al. | 128/134 |
| 3,650,523 | 3/1972 | Darby | 128/134 |
| 3,897,777 | 8/1975 | Morrison | 128/133 |
| 4,058,112 | 11/1977 | Johnson | 128/133 |

Primary Examiner—Lawrence W. Trapp
Attorney, Agent, or Firm—Arthur V. Doble

[57] ABSTRACT

A head-restraining and safety support device for use with a body splint/litter apparatus, the apparatus having a head-rest section at one end thereof. This invention includes the use of a durable, lightweight, three-section cushion which may be used to effectively cover and restrain, for the purpose of safety, the head of an accident victim who is being placed on the body splint/litter apparatus preparatory to being transported to a medical facility. Two flexible attaching members are connected to the rear edges of the opposing side cushion sections. The attaching members are fastenable to the head section of the body/splint litter apparatus by any convenient fastener such as hooks, snaps or ties, but preferably by the use of velcro fastening means. A main forehead strap protects and restrains the head from forward motion and a chin strap provides additional restraint and support, both straps being secured by any convenient means at one end of each to the front edge of one side of the cushion member, and fastenable by any convenient means to the outer surface of the opposite cushion section.

9 Claims, 4 Drawing Figures

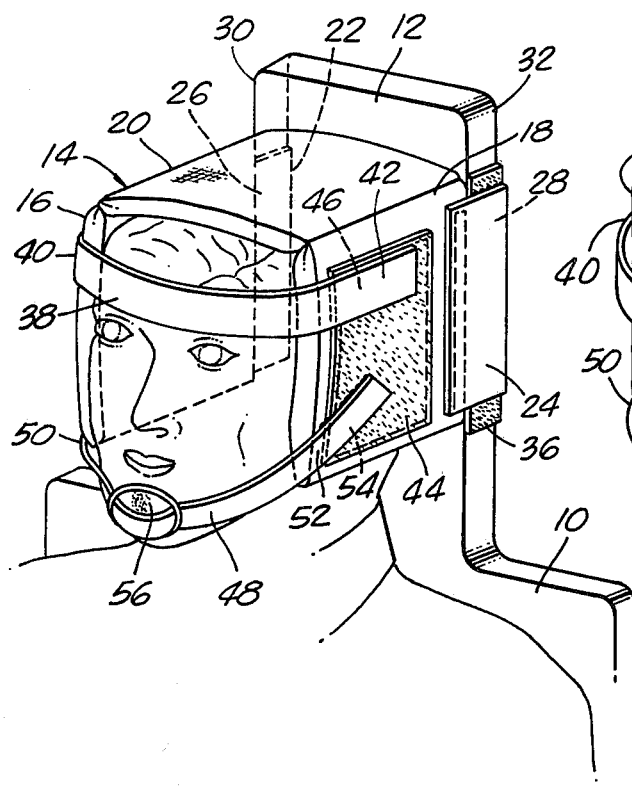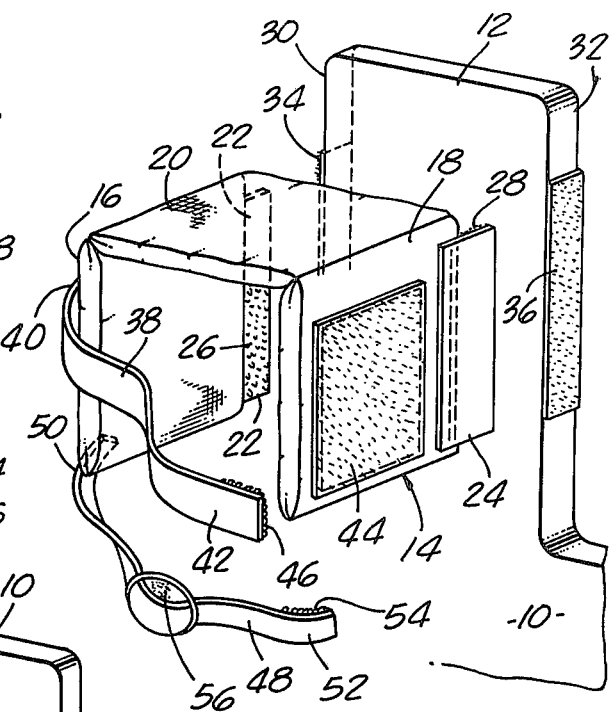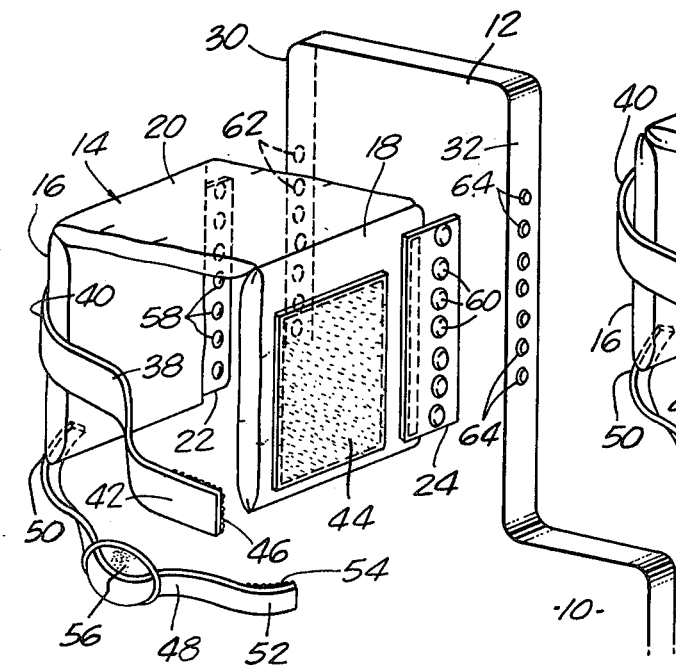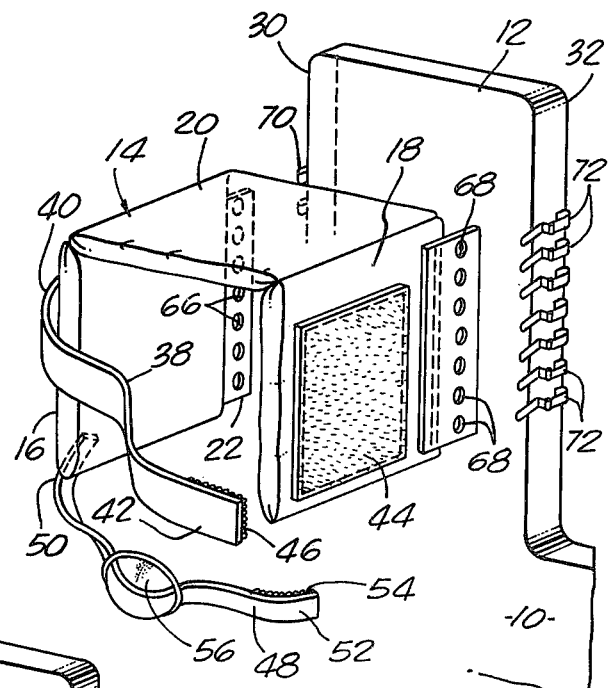

HEAD HARNESS DEVICE

BACKGROUND OF THE INVENTION

1. Field of the Invention

This invention relates to equipment for the protective emergency handling of an accident victim preparatory to being transported to an appropriate medical facility.

It more particularly relates to a head harness device for restraining an accident victim's head against injurious motion and protectively cushioning the head from external forces while the victim is being transported.

2. Description of the Prior Art

Numerous devices for restraining the motion of the head in emergency and general medical applications have been used over the years. These devices are generally used in conjunction with a body splint apparatus of some type as an adjunct thereto whereby care of the full spinal column, neck and head are facilitated. More refinements and improvements were developed with the passage of time as it become clearer that extreme caution was necessary in any attempted movement of an injured accident victim.

Emergency and other medical personnal have determined that keeping an injured accident victim immobile during handling and movement to a medical facility was imperative. Various arrangements of straps have been among the first and most common head restraining devices. Although strap arrangements have seen extensive use in emergency and other medical applications, they generally did not provide protection from external forces, were not always rapidly adjustable to the head size and location of persons being handled, were generally awkward, abrasive, uncomfortable, and few could be rapidly placed in position.

The following U.S. Pat. Nos. which represent the most pertinent art known to applicant clearly illustrate the novelty of applicant's invention: 3,151,343, 3,732,863, 3,611,454, 3,737,923, 3,707,734, 3,889,668.

Emergency and other medical personnel have long sought improved devices for the proper, safe and rapid handling of the head of an accident victim. The above prior patents did not seem to disclose the answer for which these personnel were searching.

The prior art patents disclosed the strap and web arrangements and other adjustable harnesses, and even some cushions, but none of which were ideally suited for providing the full protection, safety and comfort as taught by the invention of the applicant herein.

SUMMARY OF THE INVENTION

Applicant herein has conceived of an improved head harness device, for use with a body/splint apparatus, for rapidly, safely, comfortably and securely restraining the head of an accident victim against lateral motion at the accident site from a time prior to and while transporting the injured party from said site to a medical facility for appropriate care and treatment.

This improved head harness device includes the use of a durable, light-weight, three-section cushion which may be used for protectively and comfortably covering the top and sides of the head and restraining the motion of the head of the injured party who is being placed on a body splint/litter apparatus preparatory to being transported to a medical facility. The head harness further includes the use of flexible members attached to the side segments of the cushion, the flexible members having suitable fastener parts situated on one surface of each for rapid attachment to corresponding mating fastener parts located on the head-rest section of the body splint/litter apparatus.

To provide restraint against forward motion of the head, a strap, referred to as a forehead strap is positioned for rapid placement across a victim's forehead. One end of the strap is fixedly secured to one of the side sections of the cushion and the other end is removably fastenable to the other side by any common suitable means such as velcro fasteners. Another strap is located across the chin, and with the use of a slideably mounted chin cup, abrasion is minimized, and the head is further restrained from forward and even rotational motion. This latter strap, referred to as the chin strap, is also fastened to the side sections of the cushion in the same manner as the forehead strap.

The present invention shows several features of novelty over the known prior art, including the capability of restraining the motion of the head, restraining it with the least degree of discomfort to the injured accident victim, and protecting his head from external forces while moving him under emergency conditions which frequently may be dangerous and awkward.

It is therefore an object of this invention to provide a head harness device for restraining in all directions the motion of the head of an accident victim, when placed on a body/splint apparatus for transportation to a medical facility.

It is another object of this invention to provide a head harness which provides the least degree of discomfort to the injured victim's head when the victim is placed on a body splint/litter apparatus.

It is another object of this invention to provide protection to the injured victim's head from external forces, such as bumping into any object while being transported on a body splint/litter apparatus, from the accident site to a medical facility.

It is another object of this invention to provide a head harness device which may be instantly adjusted to any size head of an injured party and under any relative proper location of the party on a body splint/litter apparatus.

It is another object of this invention to provide a head harness device which may also be instantly attached to a body splint/litter apparatus.

It is still a further object of this present invention to provide an improved head harness device that is economical to manufacture and use, as well as being durable, rugged, reliable, lightweight and easy to use and rapidly adjustable through the use of a three-section cushion, its fastening members, adjustable restraining straps and a chin cup.

For a better understanding of this present invention, together with other and further objects thereof, reference is made to the following description taken in connection with the accompanying drawings in which preferred embodiments of this invention are illustrated, the scope of the invention being pointed out and contained in the appended claims.

BRIEF DESCRIPTION OF THE DRAWINGS

FIG. 1 is a perspective view of one embodiment of an improved head harness device using velcro fasteners with mating fasteners on the head section of a body splint/litter apparatus.

FIG. 2 is another perspective view of the head harness device in alignment with, but not attached to the head-rest section of the body panel to illustrate the velcro surfaces on the sides of the head-rest section.

FIG. 3 is a perspective view of the improved head harness device using common snap fasteners with mating snap fastener sections on the head section of a body splint/litter apparatus.

FIG. 4 is a perspective view of an improved head harness device using buckle fasteners with mating fastener sections on the head section of a body splint/litter apparatus.

DESCRIPTION OF THE PREFERRED EMBODIMENTS

In FIG. 1 there is shown a preferred embodiment of this improved head harness invention. At 10 there is shown a portion of a body-shaped panel of a body splint/litter apparatus having a head-rest section 12. Panel 10 serves as the main supporting member of the body splint/litter apparatus. A foldable three-section cushion 14 for comfortably restraining lateral motion of the head and for protecting the head against external forces is adapted for placement over the head of an accident victim who has been placed on the body-shaped panel 10 in preparation for movement and transportation to a medical facility. Cushion 14 consists of right side pad 16, left side pad 18 and top pad 20 which are foldably connected together. As may be seen by referring to both FIGS. 1 and 2, securing means, which in this embodiment are members 22 and 24, are attached to pads 16 and 18, respectively. Fastener segments, which in this embodiment are inner surfaces 26 and 28 of members 22 and 24, which are arranged for contact with surfaces 30 and 32 of head-rest section 12, are lined with velcro fasteners. Surfaces 30 and 32 of head-rest 12 are also lined with mating fastener segments, which in this embodiment are surfaces 34 and 36, for rapid and secure attachment of cushion 14 to head-rest section 12. The vertical height of each of said velcro fastener surfaces is sufficient so as to enable cushion 14 to be vertically located in its optimum position with respect to any size accident victim.

A first flexible strap means, which in this embodiment is a forehead strap 38, is attached at one end 40 thereof to right side pad 16, by any convenient means and is removably attachable at its opposite end 42 to left side pad 18 with the use of velcro fastener surface 44 on pad 18 and velcro fastener surface 46 which is on the inner side of strap 38 at its end 42. Strap 38 is adapted rapidly and adjustably for restraining forward motion of the head of an accident victim who has been placed on panel 10.

A second flexible strap means, which in this embodiment is a chin strap 48, is attached at one end 50 thereof to right side pad 16 by any convenient means, and is removably attachable at its opposite end 52 to left side pad 18 with the use of velcro fastener surface 44 on pad 18 and velcro fastener surface 54 which is on the inner side of strap 48 at its end 52. Chin strap 48 is adapted for further restraining of forward motion of the accident victim's head. A chin cup member 56 is slideably mounted on strap 48 and provides some degree of comfort to the victim's chin by preventing abrasion by strap 48 on the accident victim's chin. This chin cup member 56 also tends to provide a resistance to rotational motion of the head.

FIG. 3 depicts a further embodiment of the present invention showing another arrangement for fastening the head-harness to the head-rest section 12, which, in this instance is a series of snaps having a multiple number of snap sections 58 and 60 located on members 22 and 24, with mating snap-fastening sections 62 and 64 located on surfaces 30 and 32 of head-rest section 12 of panel 10.

FIG. 4 depicts still a further embodiment of the present invention showing another arrangement for fastening the head harness to the head-rest section 12, which in this instance is a series of buckle fasteners having a multiple number of buckle sections 66 and 68 located on members 22 and 24, with mating buckle fastener sections 70 and 72 located on surfaces 30 and 32 of head-rest section 12 of panel 10.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An improved head harness device, for use with a body splint/litter apparatus having a head-rest section at one end thereof, said head harness device comprising:
    (a) protective means for cushioning the head of an accident victim and for restraining lateral motion of the accident victim's head, said protective means having a plurality of cushion pads foldably connected together for ease of placement over the top and left and right sides of the head of said victim;
    (b) securing means, in cooperative association with said protective means, for removably securing said protective means to the head-rest section of the body splint/litter apparatus; and
    (c) restraining means, in cooperative association with said protective means, for restraining forward motion of the head of an accident victim who has been placed upon the body splint/litter apparatus, whereby the accident victim's head is restrained against injurious motion and is protectively cushioned from external forces while being transported after being placed on the body splint/litter apparatus.

2. The improved head harness device of claim 1, above, wherein the restraining means for restraining the forward motion of the head comprises a flexible strap connected at one of its ends to one of the side cushion pads and removably connected at its other end to the other side cushion pad.

3. The improved head harness device of claim 1, above, wherein the restraining means for restraining the forward motion of the head comprises a first flexible strap means to cover the forehead of an accident victim, said first flexible strap means being connected at one of its ends to one of the side cushion pads and removably connected at its other end to the other side cushion pad; and second flexible strap means to be placed beneath the chin of the accident victim, said second flexible strap means being connected at one of its ends to one of the side cushion pads and removable connected at its other end to the other side cushion pad.

4. The improved head harness device of claim 3, above, wherein the means for restraining the forward motion of the head comprises a chin cup member slideably mounted on said second flexible strap means to protect the chin of the accident victim against abrasion by said second strap means and to restrain rotational motion of the victim's head.

5. The improved head harness device of claim 1, above wherein the securing means comprises:
   (a) a pair of members which are connected to the cushion pads placed at the sides of the head of the accident victim;
   (b) fastener segments connected to each of said members; and
   (c) mating fastener segments connected to the head-rest section of the body splint/litter apparatus for securing said members and cushion pads to the head-rest section of the body splint/litter apparatus.

6. The improved head harness device of claim 5, above, wherein the fastener segments and mating fastener segments are, respectively, opposing Velcro fastener surfaces.

7. The improved head harness device of claim 5, above, wherein the fastener segments and mating fastener segments are, respectively, matching sections of common snap devices.

8. The improved head harness device of claim 5, above, wherein the fastener segments and mating fastener segments are, respectively, matching sections of common buckle devices.

9. An improved head harness device, for use with a body splint/litter apparatus having a head-rest section at one end thereof, said head harness device comprising:
   (a) a plurality of cushion pads foldably connected together for ease of placement over the top, left, and right sides of the head of an accident victim who has been placed upon the body splint/litter apparatus;
   (b) a pair of members which are connected to the cushion pads placed at the sides of the head of an accident victim;
   (c) velcro fastener surfaces mounted upon said members;
   (d) mating velcro fastener surfaces mounted on the head-rest section of the body splint/litter apparatus for securing said members and cushion pads to the head-rest section of the body splint/litter apparatus;
   (e) first flexible strap means to cover the forehead of an accident victim, said first flexible strap means being connected at one of its ends to one of the side cushion pads and removably connected at its other end to the other side cushion pad;
   (f) second flexible strap means to be placed beneath the chin of the accident victim, said second flexible strap means being connected at one of its ends to one of the side cushion pads and removably connected at its other end to the other side cushion pad; and
   (g) a chin cup member slideably mounted on said second flexible strap means to protect the chin of the accident victim against abrasion by said second strap means and to restrain rotational motion of the victim's head.

* * * * *